US007941221B2

(12) United States Patent
Foley

(10) Patent No.: US 7,941,221 B2
(45) Date of Patent: May 10, 2011

(54) METHOD AND APPARATUS FOR INTENTIONAL IMPAIRMENT OF GASTRIC MOTILITY AND/OR EFFICIENCY BY TRIGGERED ELECTRICAL STIMULATION OF THE GASTROINTESTINAL TRACT WITH RESPECT TO THE INTRINSIC GASTRIC ELECTRICAL ACTIVITY

(75) Inventor: Stephen T. Foley, Blairstown, NJ (US)

(73) Assignee: Medtronic, Inc., Minneapolis, MN (US)

( * ) Notice: Subject to any disclaimer, the term of this patent is extended or adjusted under 35 U.S.C. 154(b) by 1090 days.

(21) Appl. No.: 10/782,087

(22) Filed: Feb. 19, 2004

(65) Prior Publication Data
US 2004/0162595 A1  Aug. 19, 2004

Related U.S. Application Data

(63) Continuation of application No. 09/963,149, filed on Sep. 25, 2001, now abandoned.

(60) Provisional application No. 60/235,660, filed on Sep. 26, 2000.

(51) Int. Cl.
*A61N 1/36* (2006.01)
(52) U.S. Cl. ............ 607/40; 607/41; 607/133; 607/138
(58) Field of Classification Search .................... 607/40, 607/41, 133, 138
See application file for complete search history.

(56) References Cited

U.S. PATENT DOCUMENTS

| | | |
|---|---|---|
| 2,865,376 A | 12/1958 | Pellier et al. |
| 3,760,812 A | 9/1973 | Timm et al. |
| 4,444,207 A | 4/1984 | Robicsek |
| 4,475,560 A | 10/1984 | Tarjan et al. |
| 4,524,771 A | 6/1985 | McGregor et al. |

(Continued)

FOREIGN PATENT DOCUMENTS
DE  44 02 058  4/1995
(Continued)

OTHER PUBLICATIONS

International Search Report for PCT/US01/29892 dated Mar. 13, 2002, (4 pgs.).

(Continued)

*Primary Examiner* — Niketa I Patel
*Assistant Examiner* — Rex Holmes
(74) *Attorney, Agent, or Firm* — Shumaker & Sieffert, P.A.

(57) ABSTRACT

A sensor based gastric stimulator system and method for gastric stimulation of a patient employing an implantable gastric stimulator, which includes an information processor, an electrical stimulator circuit, and telemetry circuitry. The implantable stimulator senses intrinsic, gastric electrical activity (slow waves and/or peristaltic waves) and delivers electrical stimulation to intentionally disrupt or disorganize that activity. The stimulation is triggered by (tracks) normal gastric electrical activity and can be delivered with a spatial offset to anticipate the propagating gastric electrical activity or may be delayed temporally to anticipate the next propagating slow or peristaltic wave. The stimulator may be programmed to disrupt/disorganize all or a percentage of the intrinsic, normal gastric electrical activity. The programmer (via radio frequency data link) may non-invasively program stimulation parameters and intervals. The stimulator may provide stimulation to one or a plurality of stimulation sites and may incorporate one or a plurality of independently programmable sensing and/or stimulation channels. The information processor of the implantable gastric stimulator uses the gastric stimulation information from the non-electrode sensor for determining periods or windows of susceptibility for application of the electrical signals conveyed with the stimulation electrode for conveying electrical signals from the electrical stimulator circuit to the stomach wall of the patient.

35 Claims, 16 Drawing Sheets

IGS SYSTEM COMPONENTS

U.S. PATENT DOCUMENTS

| | | | |
|---|---|---|---|
| 4,901,722 A | | 2/1990 | Noguchi |
| 5,059,207 A | | 10/1991 | Shah |
| 5,100,431 A | | 3/1992 | Buster et al. |
| 5,188,104 A | * | 2/1993 | Wernicke et al. ............... 607/40 |
| 5,217,471 A | | 6/1993 | Burkhart |
| 5,242,458 A | | 9/1993 | Bendel et al. |
| 5,263,480 A | | 11/1993 | Wernicke et al. |
| 5,292,344 A | * | 3/1994 | Douglas ............................ 607/40 |
| 5,423,872 A | * | 6/1995 | Cigaina ............................ 607/40 |
| 5,423,876 A | | 6/1995 | Camps et al. |
| 5,433,728 A | | 7/1995 | Kim |
| 5,450,739 A | | 9/1995 | Bogart et al. |
| 5,484,404 A | | 1/1996 | Schulman et al. |
| 5,489,294 A | | 2/1996 | McVenes et al. |
| 5,540,730 A | | 7/1996 | Terry, Jr. et al. |
| 5,690,691 A | * | 11/1997 | Chen et al. ....................... 607/40 |
| 5,716,392 A | | 2/1998 | Bourgeois et al. |
| 5,836,994 A | | 11/1998 | Bourgeois |
| 5,861,014 A | | 1/1999 | Familoni |
| 5,995,872 A | | 11/1999 | Bourgeois |
| 6,026,326 A | | 2/2000 | Bardy |
| 6,041,258 A | | 3/2000 | Cigaina et al. |
| 6,083,249 A | | 7/2000 | Familoni |
| 6,091,992 A | | 7/2000 | Bourgeois et al. |
| 6,097,984 A | | 8/2000 | Douglas |
| 6,098,672 A | | 8/2000 | Kiholm |
| 6,104,955 A | | 8/2000 | Bourgeois |
| 6,115,635 A | | 9/2000 | Bourgeois |
| 6,146,391 A | | 11/2000 | Cigaina |
| 6,216,039 B1 | * | 4/2001 | Bourgeois ....................... 607/40 |
| 6,238,423 B1 | * | 5/2001 | Bardy ............................. 607/40 |
| 6,243,607 B1 | | 6/2001 | Mintchev et al. |
| 6,321,124 B1 | | 11/2001 | Cigaina |
| 6,327,503 B1 | * | 12/2001 | Familoni ......................... 607/40 |
| 6,449,511 B1 | | 9/2002 | Mintchev et al. |
| 6,453,199 B1 | | 9/2002 | Kobozev |
| 6,510,332 B1 | | 1/2003 | Greeenstein |
| 6,542,776 B1 | | 4/2003 | Gordon et al. |
| 6,571,127 B1 | | 5/2003 | Ben-Haim et al. |
| 6,591,137 B1 | | 7/2003 | Fischell et al. |
| 6,600,953 B2 | | 7/2003 | Flesler et al. |
| 6,606,523 B1 | | 8/2003 | Jenkins |
| 6,615,084 B1 | | 9/2003 | Cigaina |
| 6,678,561 B2 | | 1/2004 | Forsell |
| 6,895,278 B1 | * | 5/2005 | Gordon ............................ 607/40 |
| 7,177,693 B2 | | 2/2007 | Starkebaum |
| 2002/0072780 A1 | | 6/2002 | Foley |
| 2002/0161414 A1 | | 10/2002 | Flesler et al. |
| 2002/0198470 A1 | | 12/2002 | Imran et al. |
| 2003/0009202 A1 | | 1/2003 | Levine |
| 2003/0018367 A1 | | 1/2003 | DiLorenzo |
| 2003/0054463 A1 | | 3/2003 | Baker et al. |
| 2004/0088022 A1 | | 5/2004 | Chen |
| 2004/0193229 A1 | | 9/2004 | Starkebaum et al. |
| 2004/0236381 A1 | | 11/2004 | Dinsmoor et al. |
| 2004/0236382 A1 | | 11/2004 | Dinsmoor et al. |
| 2005/0033375 A1 | | 2/2005 | Marchal et al. |
| 2005/0137643 A1 | | 6/2005 | Mintchev |
| 2005/0149141 A1 | | 7/2005 | Starkebaum |
| 2005/0209653 A1 | | 9/2005 | Herbert et al. |
| 2005/0222638 A1 | | 10/2005 | Foley et al. |

FOREIGN PATENT DOCUMENTS

| | | |
|---|---|---|
| WO | WO 97/41921 | 11/1997 |
| WO | WO 02/087657 | 11/2002 |

OTHER PUBLICATIONS

International Preliminary Examination Report for PCT/US01/29892 dated Jan. 6, 2003, (3 pgs.).

Chen et al. "Electrical Pacing Accelerates Intestinal Transit Slowed by Fat-Induced Ileal Brake," Digestive Diseases and Sciences, vol. 48, No. 2 (Feb. 2003), pp. 251-256.

Lin et al., "Electrical Stimulation of the Small Intestine in Dogs," Proceedings, 19$^{th}$ International Conference, IEEE/EMBS, (Oct. 30-Nov. 2, 1997), Chicago, IL pp. 1803-1806.

Sun et al. "Intestinal Electric Stimulation Decreases Fat Absorption in Rats: Therapeutic Potential for Obesity," Obesity Research, vol. 12, No. 8 (Aug. 2004), pp. 1235-1242.

"Implantable Gastric Stimulation for the Treatment of Morbid Obesity," by Valerio Cigaina, Transneuronix, Inc., Mt. Arlington, New Jersey, Revision 2, Nov. 1, 1999 (11 pp).

"Implantable Gastric Stimulation for the Treatment of Morbid Obesity," by Valerio Cigaina, Transneuronix, Inc., Mt. Arlington, New Jersey, Revision 1, Oct. 3, 1999 (12 pp).

Dickens et al., "Identification of rhythmically active cells in guinea-pig stomach," Journal of Physiology, vol. 514, No. 2, pp. 515-531 (Jan. 1999).

Huizinga, "Gastrointestinal Peristalsis: Joint Action of Enteric Nerves, Smooth Muscle, and Interstitial Cells of Cajal," Microscopy Research and Technique, vol. 47, No. 4, pp. 239-247 (Dec. 1999).

Vantrappen et al., "Gastrointestinal Motility Disorders," Digestive Diseases and Sciences, vol. 31, No. 9, pp. 5S-25S, (Sep. 1986 Supplement).

Supplemental European Search Report dated May 8, 2009 for corresponding European Patent Application 01973465.6-1265 (3 pgs.).

* cited by examiner

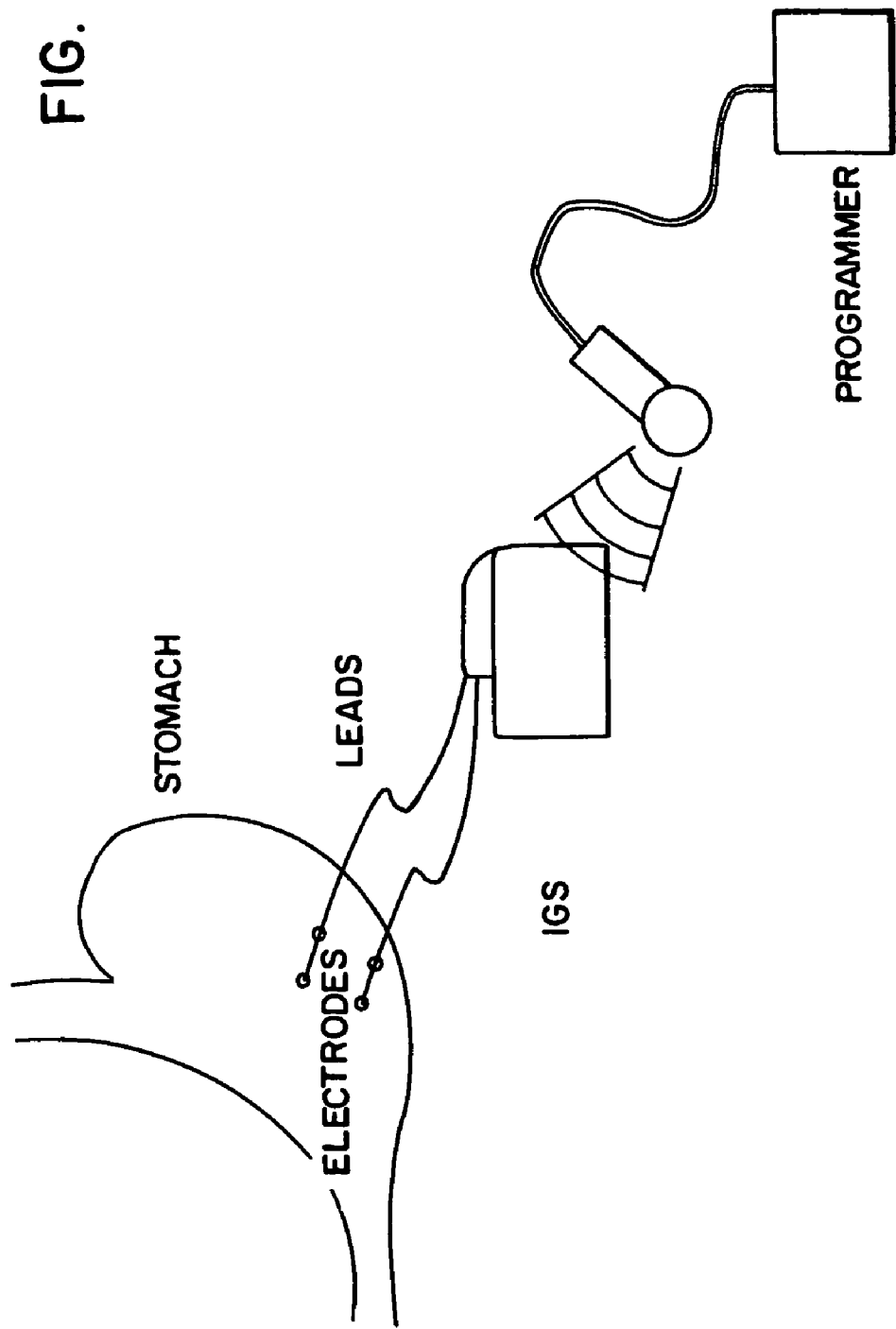

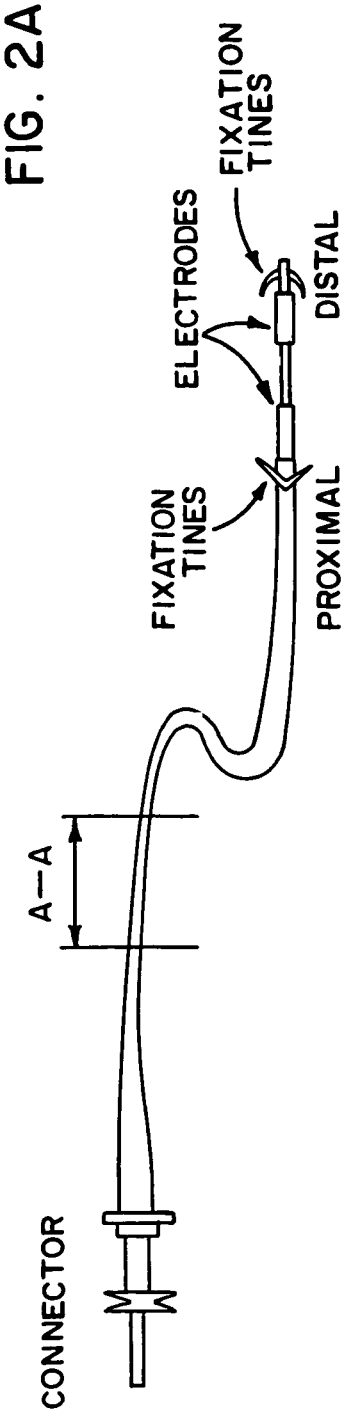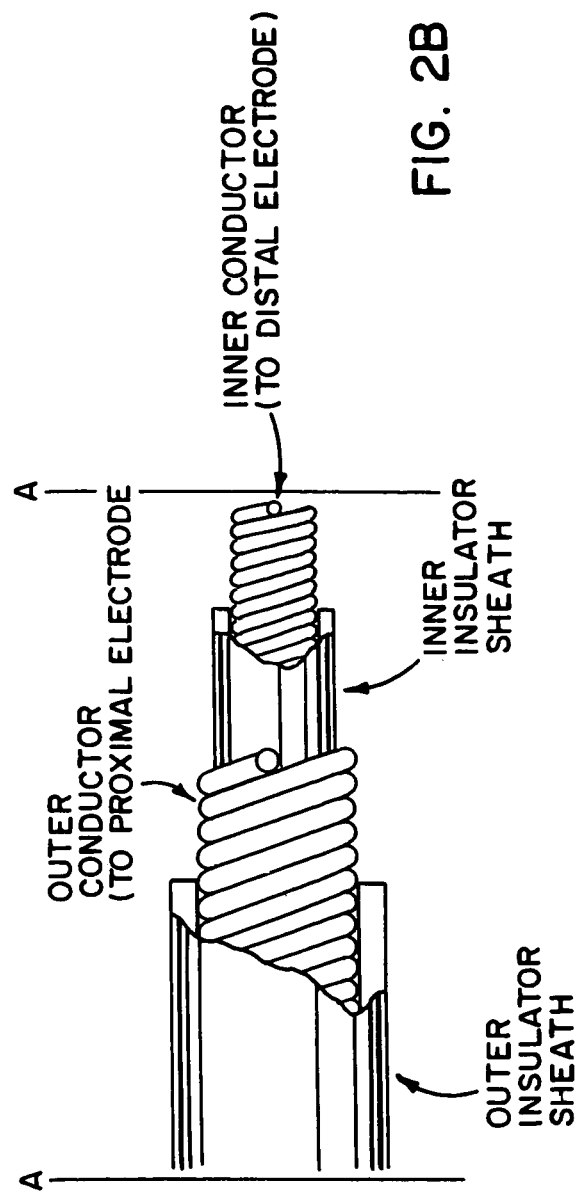

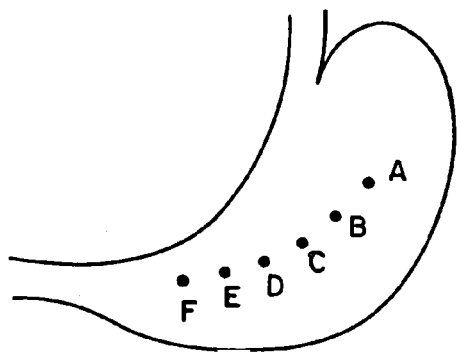
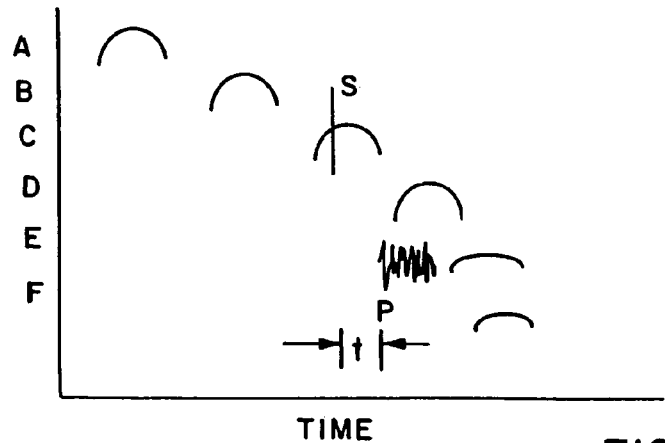
FIG. 14
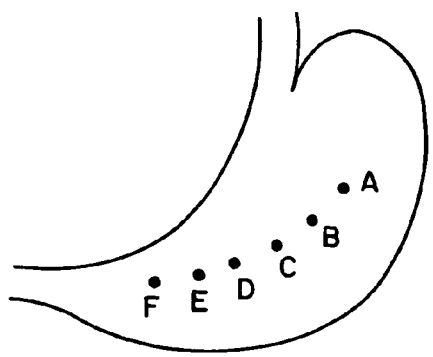
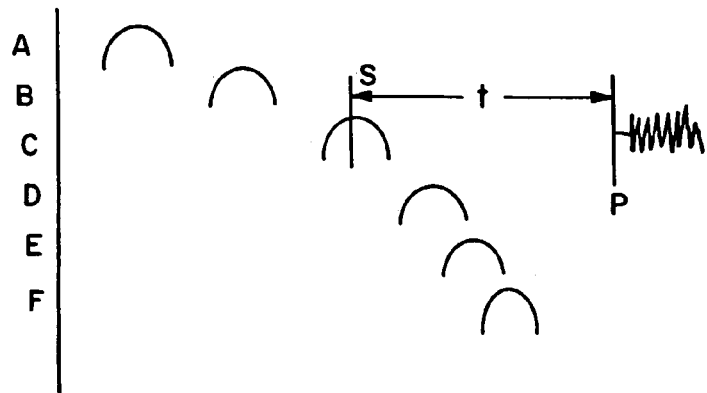
FIG. 15

METHOD AND APPARATUS FOR INTENTIONAL IMPAIRMENT OF GASTRIC MOTILITY AND/OR EFFICIENCY BY TRIGGERED ELECTRICAL STIMULATION OF THE GASTROINTESTINAL TRACT WITH RESPECT TO THE INTRINSIC GASTRIC ELECTRICAL ACTIVITY

CROSS REFERENCE To RELATED APPLICATION

This application is a continuation of U.S. patent application Ser. No. 9/963,149, filed Sep. 25, 2001 now abandoned, the entire content Of which is incorporated herein by reference, and which claims benefit of U.S. Provisional Application No. 60/235,660, filed Sep. 26, 2000.

BACKGROUND OF THE INVENTION

1. Field of the Invention

The present invention relates to an implantable gastric electrical stimulator system that can be used to decrease gastric motility and/or gastric efficiency for the treatment of obesity. More particularly, the system employs an implantable electrical stimulator, one or a plurality of implant-able stimulator leads (electrodes), and an external programmer, and an algorithm used to automatically control synchronized electrical stimulation frequency, interval, amplitude, or a combination of such parameters for treatment of obesity and other eating disorders.

2. Description of the Related Art

Obesity is a major health concern in western civilization. Surveys indicate that 33% of the population is overweight with the number increasing every year. Obesity is the second leading cause of preventable death in the United States. It is associated with several comorbidities that affect almost every body system. Some of these comorbidities are: hypertension, diabetes, coronary disease, breathing disorders, and musculoskeletal problems. It is estimated that the costs associated with obesity approach $70 billion per year.

Multiple factors contribute to obesity, but the two major factors are physical inactivity and overeating. Existing therapies include diet, exercise, appetite suppressive drugs, metabolism enhancing drugs, surgical restriction of the gastric tract, and surgical modification of the gastric tract. Efficacy of these therapies range from little or no weight loss up to weight loss approaching 50% of initial body weight.

Gastroparesis is an adverse medical condition in which normal gastric function is impaired. Gastroparetic patients exhibit reduced gastric motility with accompanying symptoms of nausea and/or vomiting and gastric discomfort. They may complain of bloating or a premature or extended feeling of fullness (satiety). Typically, the condition results in reduced food intake (in portion and/or frequency) and subsequent weight loss. Physiologically, the condition may be associated with damage or neuropathy of the stomach enervation or damage or dystrophy of the stomach muscle with subsequent attenuated (in amplitude and/or frequency) peristaltic activity of the stomach muscles. Some studies indicate that it is also associated with dysrhythmias of the stomach.

An examination of the symptomology and consequences of gastro-paresis reveals some effects that could be beneficial as a therapy for obesity, if they could be mediated and modulated. This disclosure sets forth a class of implantable electrical device(s) that can potentially effect a mild, reversible form of gastroparesis by inducing electrophysiological disorganization or disruption in the normal stomach motility.

The stomach is a complex organ of the digestive tract (alimentary canal) with the primary functions of dissolution, reduction, and motility of ingested food. These typical functions are accomplished through secretion of biochemical reagents to promote dissolution; kinetic mixing movements to reduce the particle size and promote mixing; and kinetic propulsive movements to move the chyme (solution of small food particles and biochemical reagents) into the intestines. The kinetic movements of the stomach are accomplished by organized/phased contractions of the stomach wall/smooth muscle.

Normal contractions of the stomach are the result of three control components: neural activity, chemical activity, and myogenic activity.

The neural control component refers to the intrinsic and extrinsic nerves innervating the stomach. The intrinsic nerves release various neurotransmitters and peptides that control contractions and motility. Studies indicate that the extrinsic nerves may influence the contractions by the release of modulative substances.

The chemical control component refers to the various substances (neurotransmitters, neuromodulators and peptides) released from the nerve endings or endocrine-paracrine cells and glands of the stomach. These biochemical substances may act directly on the smooth muscle cell or on the nerves to modulate or control the occurrence of contractions and motility.

The myogenic control component refers to small electrical oscillations of the smooth muscle cells related to polarization and depolarization of the smooth muscle cells. The myogenic activity is referred to as electrical control activity or slow waves.

The slow wave is the underlying clock for peristaltic activity. Slow waves are omnipresent and typically occur at frequencies of 2-4 cycles per minute. All slow waves are not linked to contractions, but a normal peristaltic contraction must occur in synchrony with a slow wave.

To initiate normal peristaltic contractions, multiple control means must be present. The slow wave (resulting from the cell membrane potential depolarization) provides the basic timing/interval and organization. However, the strength of the typical slow wave depolarization alone is not sufficient to exceed the excitation threshold required to initiate the smooth muscle contraction. A neural or chemical component must also be present to augment the myogenic activity. When a neural and/or chemical component is present, the depolarization strength exceeds the excitation threshold and a contraction occurs. (The contraction results in additional electrical activity referred to as electrical response activity or action potentials.)

However, initiating the contraction is only part of the peristaltic activity. To be physiologically effective (efficiently reduce, mix and/or propulse the stomach contents), the contraction must propagate in an organized, phased manner in three dimensions and in time (across and/or along the various muscle layers of the stomach).

Typically, the contraction involves the circular and longitudinal muscle layers of the stomach wall. Contraction of the circular smooth muscle layer decreases the lumen diameter. Contraction of the longitudinal muscle layer decreases the length of the stomach and may serve to assist in expansion of the lumen adjacent to the contracted circular muscle layer and to propagate the contraction to the neighboring uncontracted segment of the circular muscle. Coordinated contraction between both muscle layers is necessary for peristaltic propagation.

Intentional interference with any or all of the three control components and/or the coordination of the contraction propagation may impair the contraction and its associated kinetic function. Electrophysiologically, the interference may be administered as any one or combination of the following:

(a) electrical stimulation that induces asynchronous depolarization of individual cells or small groups of cells just prior to (spatially or temporally) or during a slow wave or peristaltic wave creating disorganization/attenuation of the wave;

(b) electrical stimulation that induces synchronous depolarization of a large area of cells prior to a slow wave or peristaltic wave creating an area that is refractory to the wave (may also induce a contraction);

(c) persistent electrical stimulation of the stomach nerves creating a neural desensitization, suppression or blocking of the stimulated area;

(d) electrical stimulation that entrains the slow wave at a frequency greater than 4 cpm creating a tachygastria condition so that peristalsis does not occur;

(e) electrical stimulation that entrains the slow wave at a frequency that competes with the intrinsic frequency but originates at a different location(s) creating competing ectopic waves; and (f) temporally or spatially segregated, directional electrical stimulation of the individual muscle layers creating decoupling of the peristaltic coordination.

Additional methodologies may also accomplish the same ends, but may not be as easily applied, may require iterative or multiple applications or may be difficult to reverse. These additional methods include:

(a) creation of gastric smooth muscle lesions by ablative techniques (radio frequency, microwave, cryogenic) to lessen the contractility of the muscle or to change the contraction vector to a less efficient direction/sequence; and (b) administration of precise doses and patterns of intramuscular paralytic agents (e.g. botulism toxin, curare, etc.) to prevent the affected areas from contracting and/or to force a contraction along a specific less efficient path.

These items are discussed in separate disclosures. This disclosure will focus on the electrophysiological means of impairment.

Electrical stimulation of the stomach and other portions of the gastric intestinal tract has been experimented with for some time. Most of the experimentation has been oriented toward improving the gastric emptying usually by attempting to speed up or strengthen/reinforce the peristaltic activity.

U.S. Pat. No. 5,423,872 to Cigaina for "Process and Device for Treating Obesity and Syndromes Related to Motor Disorders of the Stomach of a Patient" issued Jun. 3, 1995, describes an implantable gastric electrical stimulator at the antrum area of the stomach which generates sequential electrical pulses to stimulate the entire stomach, thereby artificially altering the natural gastric motility to prevent emptying or to slow down food transit through the stomach. Cigaina however has the inherent disadvantage that it is a stimulation device solely, and does not incorporate on-demand stimulation other than that of manual cycling provided by magnetic application, which wastes energy by applying stimulation when it is not therapeutically required.

U.S. Pat. No. 5,690,691 to Chen et al. for "Gastro-intestinal Pacemaker Having Phased Multi-Point Stimulation" issued Nov. 25, 1997, describes a portable or implantable gastric pacemaker employing a number of electrodes along the greater curvature of the stomach for delivering phased electrical stimulation at different locations to accelerate or attenuate peristaltic movement in the GI tract. Chen et al. additionally provides a sensor electrode or a stimulation electrode wherein the response of an organ to an electrical stimulation pulse is sensed for delivering stimulation to a plurality of electrodes to provide phased electrical stimulation. However, Chen et al. is specifically directed to phased stimulation that progresses through the plurality of electrodes located along the peristaltic flow path and specifically senses the response of the organ to the electrical stimulation. Chen does not address sensing of the intrinsic electrical activity for the purpose of applying therapy.

U.S. Pat. No. 5,836,994 to Bourgeois for "Method and Apparatus for Electrical Stimulation of the Gastrointestinal Tract" issued Nov. 17, 1998, describes an implantable gastric stimulator which incorporates direct sensing of the intrinsic gastric electrical activity by one or more sensors of predetermined frequency bandwidth for application or cessation of stimulation based on the amount of sensed activity. The Bourgeois sensing circuitry inhibits therapy if a peristaltic wave is sensed and provides stimulation if it is not sensed. It does not apply therapy to impair gastric motility.

U.S. Pat. No. 6,091,992 to Bourgeois for "Method and Apparatus for Electrical Stimulation of the Gastrointestinal Tract" issued Jul. 18, 2000, is similar to the '994 patent. It relates to provision of separate electrical pulse trains of differing parameters wherein the pulse trains are composed of a series of at least two pulses. The therapy is applied to promote gastric peristalsis.

U.S. Pat. No. 6,104,955 to Bourgeois for "Method and Apparatus for Electrical Stimulation of the Gastrointestinal Tract" issued Aug. 15, 2000, relates to a gastric stimulator with reversion to a sensing mode to determine the intrinsic slow wave interval to prevent stimulation when the gastric tract is in inter-digestive phases. Like the previous Bourgeois patents, '955 addresses stimulation to promote gastric normalcy.

U.S. Pat. No. 5,861,014 to Familoni for "Method and Apparatus for Sensing a Stimulating Gastrointestinal Tract On-Demand" issued Jan. 19, 1999, relates to an implantable gastric stimulator for sensing abnormal electrical activity of the gastrointestinal tract so as to provide electrical stimulation for a preset time period or for the duration of the abnormal electrical activity to treat gastric rhythm abnormalities. Familoni also addresses recording of abnormal activity for a preset time period, but does not address altering of a normal gastric activity to achieve a variable result such as treatment for obesity. It does not apply therapy to disrupt normal gastric activity.

Accordingly, the known prior art relates to (1) the provision of electrical stimulation (phased or unphased) without regard to intrinsic activity, or (2) the provision of electrical stimulation to induce normal peristalsis, or (3) the provision of electrical stimulation to counteract abnormal gastric activity.

Thus, the prior art does not address the provision of electrical stimulation with regards to intrinsic gastric electrical activity for the intended purpose of disrupting normal, intrinsic gastric activity.

SUMMARY OF THE INVENTION

The present invention is directed to applying an implantable gastric stimulation (IGS) and lead system to sense intrinsic gastric electrical activity, identify that activity as normal or abnormal, and to apply electrical stimulation to the normal activity for the intended purpose of disrupting/disorganizing it.

Briefly summarized, the present invention relates to a gastric simulator system and method for gastric stimulation of a patient employing an implantable gastric stimulator, which includes an information processor, electrical stimulation circuitry, electrical sensing circuitry, electrode switching circuitry, and telemetry circuitry. A remote programmer is provided to operate with the telemetry circuit of the implantable gastric stimulator for controlling the operation of the electrical stimulator circuit with the information processor. Leads are provided between the implantable gastric stimulator and the stomach wall of the patient for stimulation and/or sensing electrodes. The stimulation electrodes are provided for conveying electrical signals from the electrical stimulator circuit to the stomach wall of the patient, while the sensor electrodes are provided for communicating intrinsic gastric electrical activity information (from the stomach wall of the patient) via the electrical sensing circuitry to the information processor. The electrode switching circuitry allows the function and polarity of each electrode to be controlled by the information processor.

BRIEF DESCRIPTION OF THE DRAWINGS

FIG. 1 illustrates the components of the IGS system;

FIGS. 2A and 2B further illustrate the stimulation lead and the construction of the lead body;

FIG. 14 depicts electrical stimulation with a spatial and temporal offset;

FIG. 15 depicts anticipatory electrical stimulation;

DETAILED DESCRIPTION OF THE PREFERRED EMBODIMENTS

The preferred embodiment of the invention consists of an implantable gastric stimulator (IGS), one or a plurality of implantable leads (two or more electrodes) that are electrically coupled to the stomach wall and the IGS, and an external programmer which can non-invasively communicate (bi-directionally) with the IGS via a radio frequency data link (see FIG. 1).

The external programmer is the interface between the physician (user) and the IGS. It consists of a transceiver to communicate with the IGS, a user interface (e.g., keyboard, tactile or soft buttons, display, and software) to provide a usable input/output method to the physician, and electronic circuitry and software to process the inputs or outputs to the appropriate format for either end (device or user). The programmer conveys information to the device and receives information from the device via a radio frequency data link. The information is conveyed as a string of data packets. In the preferred embodiment, an error checking algorithm would be utilized to determine the veracity of the string or packet.

The implantable lead consists of a connector (proximal) end that interfaces (electrically and mechanically) to the IGS, a lead body (medial portion) that is electrically continuous between the connector (proximal) electrical terminals and the electrodes, and an electrode (distal) end that interfaces with the stomach wall (reference FIG. 2A).

The connector end consists of one or a plurality of proximal electrical terminations, a means for insulation between the terminations and between the terminations and the surrounding environment, and a mechanical means for securing the connector to the IGS connection.

The lead body (medial portion) consists of an electrically continuous path between the electrode(s) and proximal electrical terminations. Typically, the path is an elongated metallic coil. The lead body can have one or a plurality of coils. The coils are insulated from each other and from the surrounding environment by an insulating sheath(s). FIG. 2B depicts a typical lead body construction. Typically, each coil is connected to a specific proximal terminal (corresponding to an IGS input/output) and a specific electrode. An alternative configuration may have multiple electrodes connected to the same coil.

Figure 3:
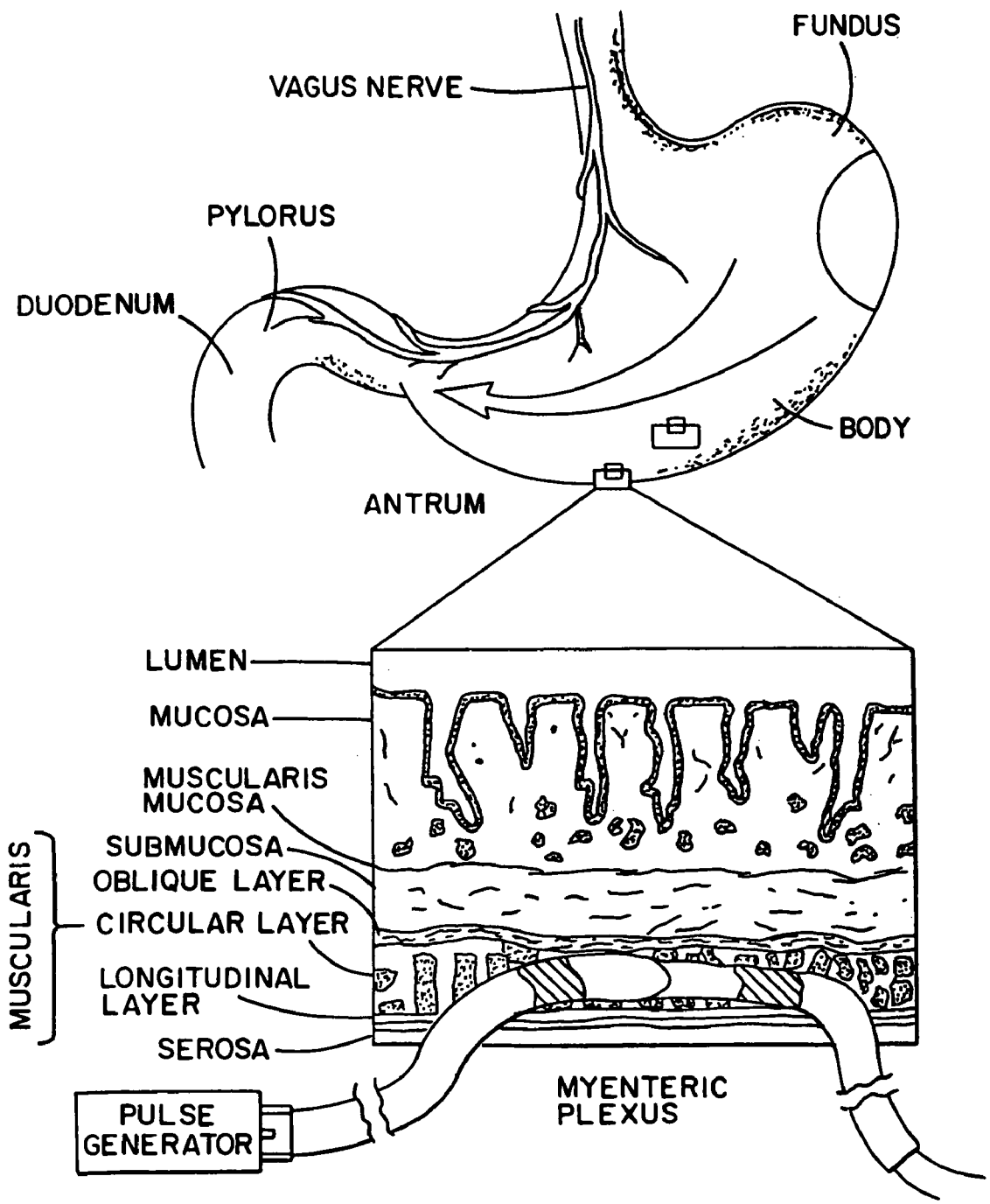
FIG. 3 shows the placement of the electrodes in the stomach.

The electrode (distal) end of the lead communicates electrically to the stomach wall. In the preferred embodiment, the electrodes are utilized in pairs to perform bipolar sensing and stimulation. However, also in the preferred embodiment, the bipolar pairs are not required to be resident on the same implantable lead (multiple monopolar leads or a combination of monopolar and multipolar leads may be used instead). The electrodes should communicate with the circular layer of the stomach smooth muscle. This communication can be effected by superficial contact with the serosa, embedding the electrode intramuscularly (within the longitudinal or circular muscle), or by sub serosal placement. FIG. 3 depicts the electrodes embedded within the circular layer. The electrode size and configuration must consider the function, the implantation location, and the stimulation parameters to be utilized. A sensing electrode should have maximum surface area to acquire the intrinsic electrical signal. A stimulation electrode should have minimal surface area to concentrate the energy density for stimulation, but must also consider the effects of dissociation of the metal due to the stimulation pulse and due to ion imbalance. Likewise, the gastric wall varies in thickness (depending on location) from 4-5 mm to greater than 1 cm with the circular and longitudinal layers comprising approximately half that thickness. Additionally, the distal end contains the means for securely attaching the electrodes to the gastric wall. The fixation mechanism of the preferred embodiment is a pair of polymer tines that oppose each other and are located on either side of the electrode(s). FIG. 2A depicts the tine configuration at the distal end of the lead. An alternative fixation embodiment is to secure the lead to the gastric wall with a suture through the tissue and around an elastomer sleeve on the lead body.

The IGS is a small, compact pulse generator. Externally, it consists of a hermetic housing and a means for electrically and mechanically connecting the lead to the internal electronics. Internally, the IGS contains electronic circuitry and a power supply (battery and/or rf energy coupling circuitry).

Figure 4:
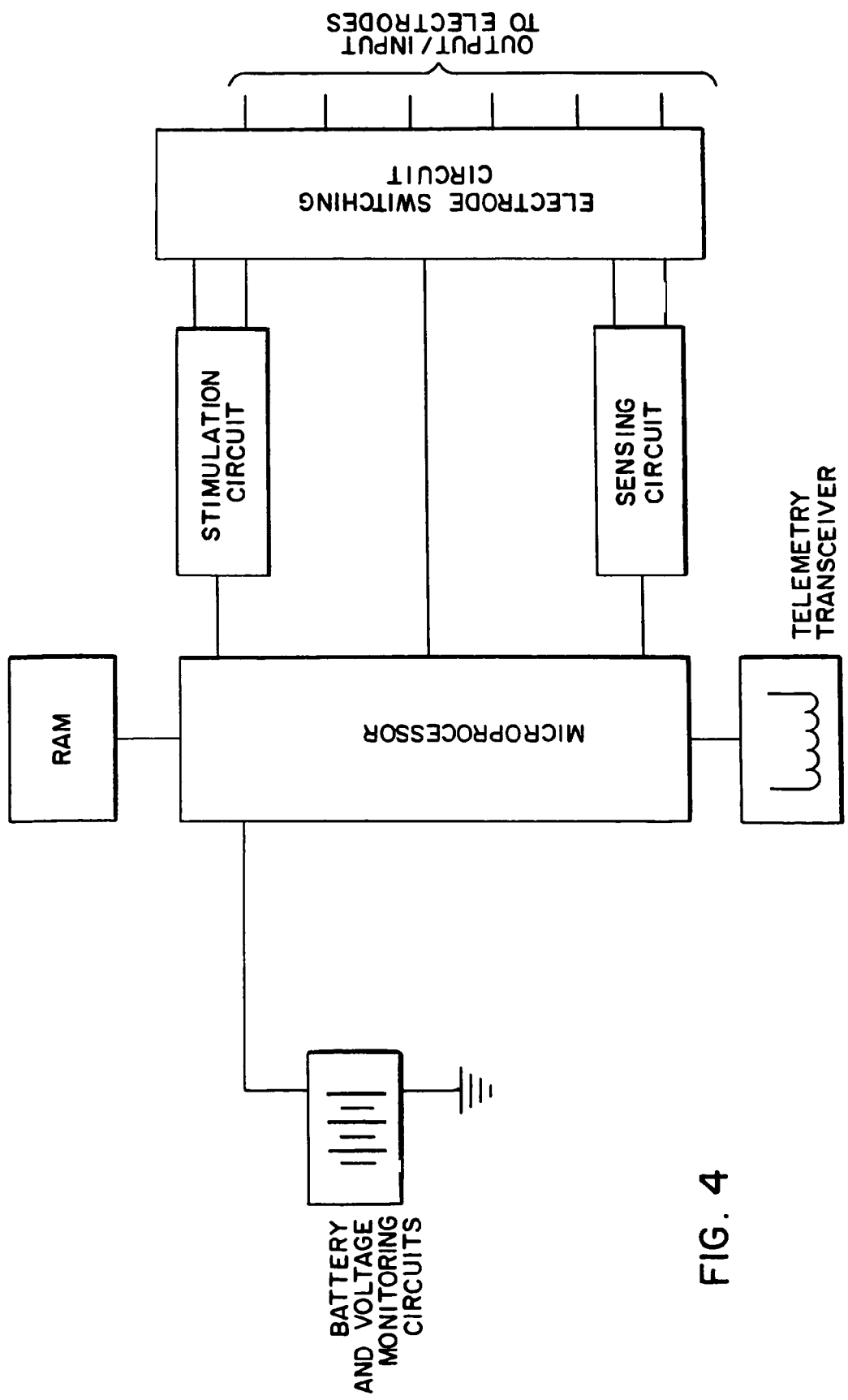
FIG. 4 shows a functional block diagram of a single channel IGS.
Figure 5:
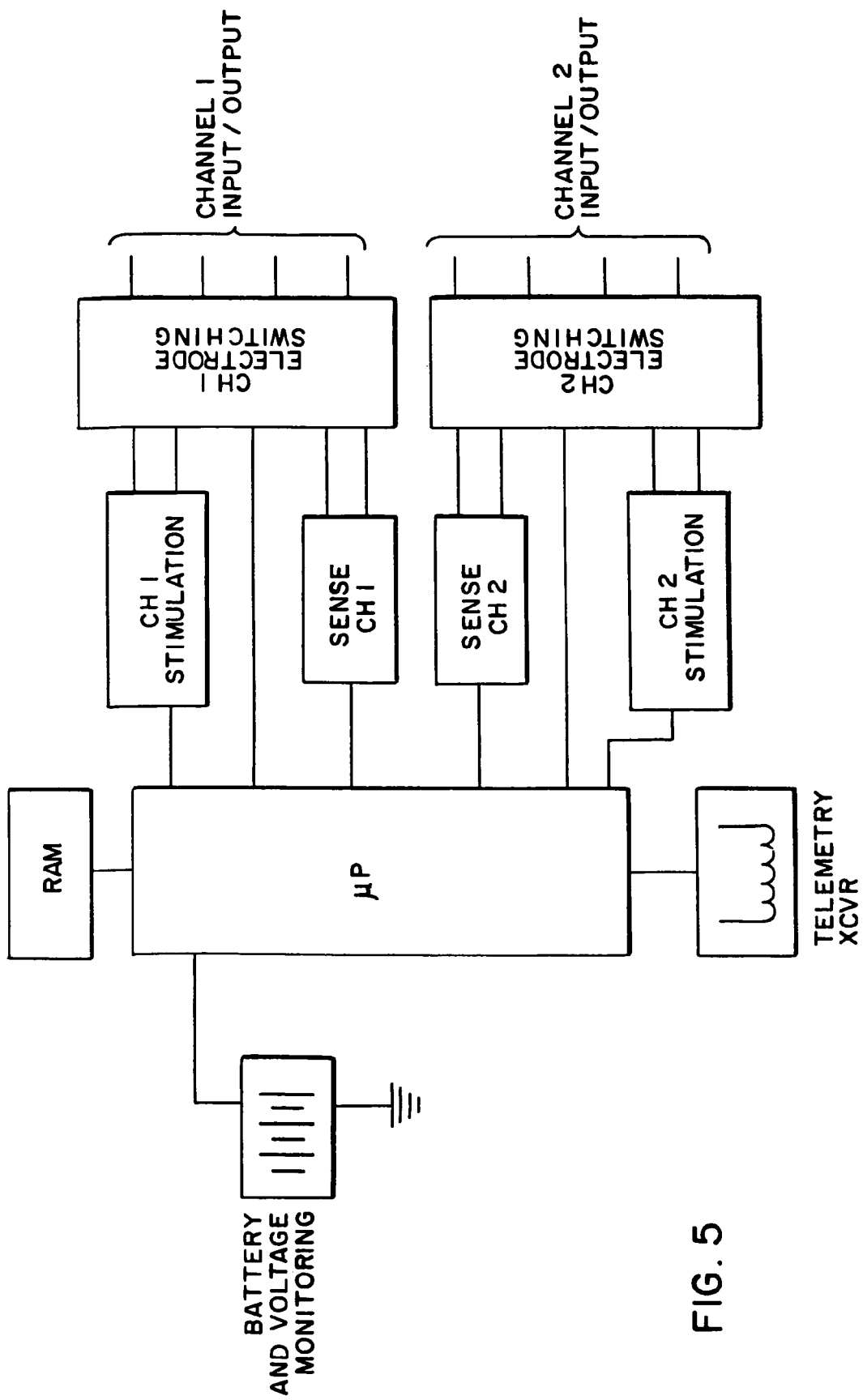
FIG. 5 shows a functional block diagram of a multi-channel.

In the preferred embodiment, the electronic circuitry consists of a microprocessor, electrical sensing (input) circuitry, electrical stimulation (output) circuitry, electrode switching circuitry, telemetry circuitry, and random access memory (reference FIG. 4). In an alternative embodiment, the IGS may have multiple sensing and/or stimulation circuits (channels) to provide more optimum sensing and stimulation to differing areas of the gastric system (reference FIG. 5).

The microprocessor is an integrated circuit that serves as an information processor that controls the IGS functions, performance, and analyses (if any). It receives inputs from the telemetry circuitry, the sensing circuitry, the RAM, and from internal functional checking. Depending upon the programming and the inputs, the microprocessor controls outputs to the telemetry circuitry, the stimulation circuitry, the RAM, and the electrode switching circuitry. The processor controls the basic timing and routing of the inputs and the output sequencing and parameters.

The sensing circuitry receives signals from the intrinsic gastric electrical activity via the selected sensing electrodes of the lead(s). The sensing input is utilized to classify the intrinsic gastric activity and as the trigger for the stimulation output. The sensing circuitry filters and amplifies the intrinsic signal and conveys it to the microprocessor. The sensing circuitry may employ a neural network approach to assist in the classification of the intrinsic gastric activity. The selection of the sensing electrodes, the timing of the sensing, and degree of amplification is controlled by the microprocessor and is programmable (via the telemetry circuitry).

The stimulation circuitry provides the electrical pulses employed for stimulation. The stimulation circuitry may invoke either a constant current approach or a constant voltage approach. In the preferred embodiment, the stimulation circuitry will provide pulses of programmable amplitude, frequency (pulses per second), and pulse width. An alternative embodiment entails the use of switching between individual capacitors in an array (switch cap technology) to provide adjacent or overlapping pulses of narrow width to achieve a continuous (or near continuous) pulse of a wider width. The stimulation circuitry is controlled by the microprocessor and is programmable.

Figure 6:
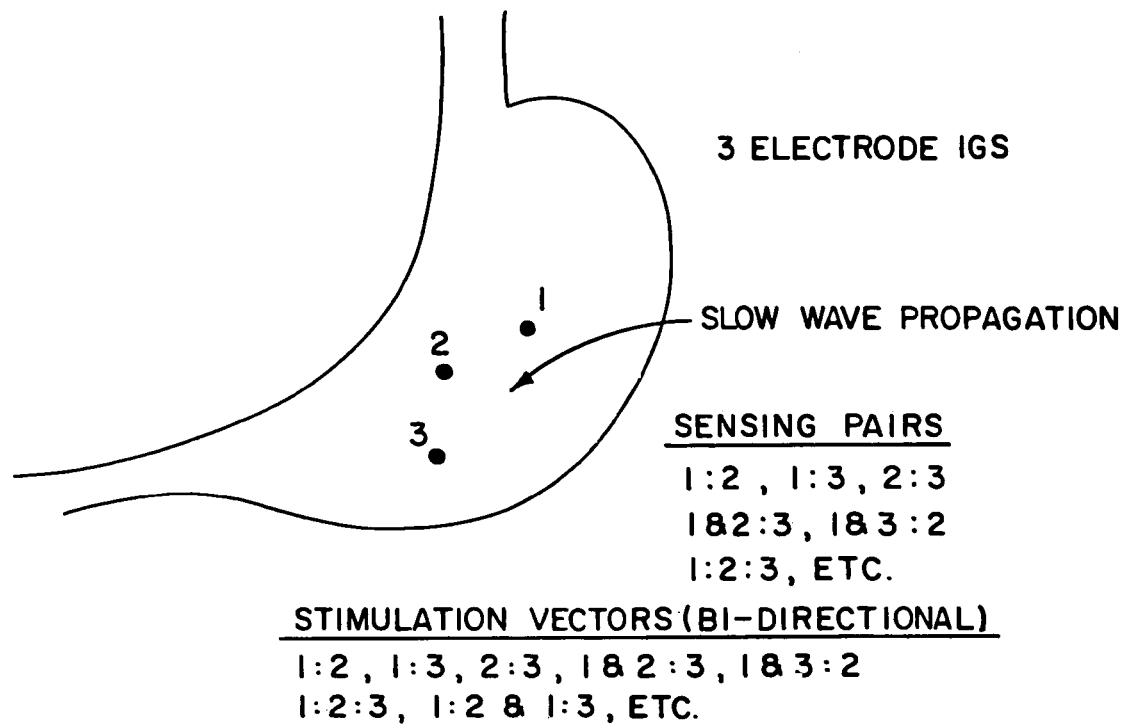
FIG. 6 illustrates possible sensing "pairs" and stimulation vectors ("pairs") of electrodes for a three electrode system.
Figure 7:
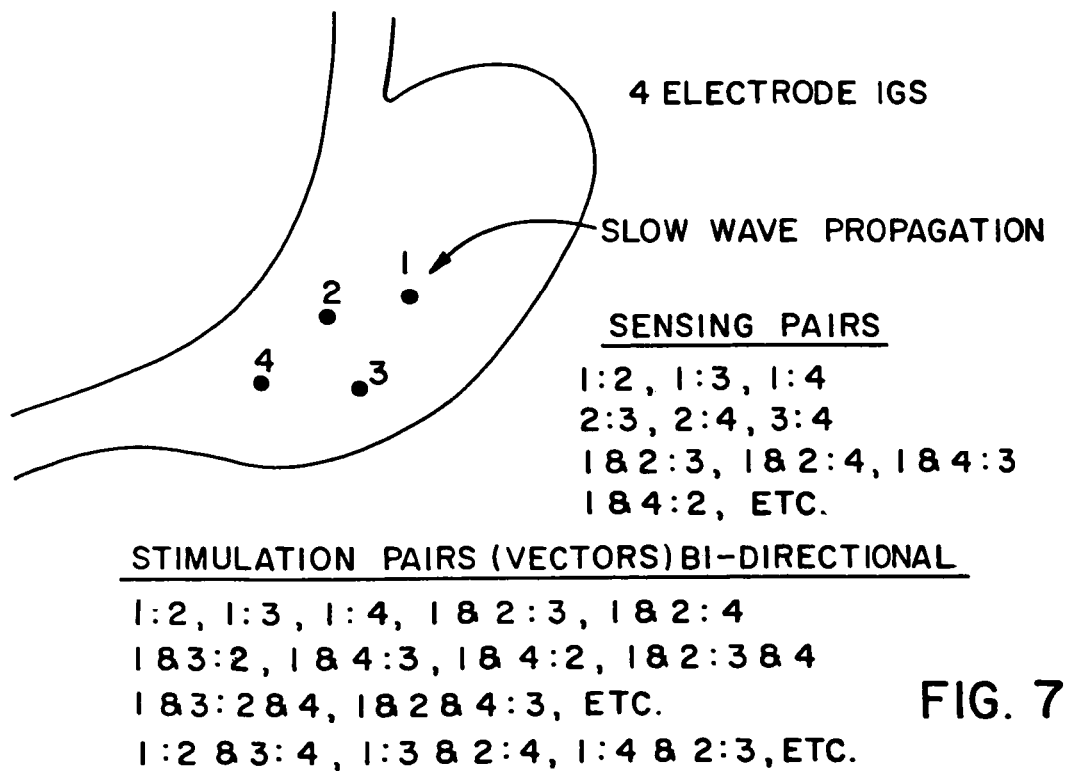
FIG. 7 illustrates possible sensing "pairs" and stimulation vectors for a four electrode system.

The electrode switching circuitry establishes the function of each electrode and the polarity of the electrode. In the preferred embodiment, the electrode switching circuitry will enable a pair of electrodes to be used for sensing, and a pair or pairs of electrodes to be used for stimulation. FIGS. 6 and 7 depict possible sensing configurations ("pairs") and possible stimulation vectors for a three and a four electrode system. The stimulation and sensing may utilize the same electrodes. During the stimulation period, the electrode switching circuitry can change the polarity of the stimulation electrodes to create multi-phasic pulses, alternating polarity between pulses or a series of pulses, and different stimulation vectors. Likewise, the switching circuitry can enable different pairs of sensing electrodes to sample gastric electrical activity at various sensing locations or along different vectors. Complex sensing patterns can be invoked to differentiate slow wave propagation direction and intervals. The switching circuitry may also include compensation (to offset internal leakage currents across the switches involved in sensing) and blanking to prevent stimulation pulses from saturating the sense amplifiers. The switching circuitry is controlled by the microprocessor and is programmable. Complex switching schemes can be stored in RAM and be activated as a program. The switching software would be designed to ensure that each configuration would have at least one bipolar pair to complete the electrical circuit.

The telemetry circuitry consists of an antenna and a transceiver. The circuitry may also include a telemetry buffer to accommodate large data transactions. The telemetry circuit transmits and receives pulses to and from the programmer. The circuitry may employ amplitude modulation, frequency modulation, or pulsed modulation at radio frequencies. In the preferred embodiment, the telemetry would have a range of several inches to allow for deep implantation of the IGS. The telemetry string would utilize an initiation protocol to establish two way communication, an identity packet to provide device/programmer identification, multiple information or programming packets to communicate the requisite data, error checking of the packets (cyclic redundancy checking or check sums) to ensure accuracy of the information, and a termination protocol to signal the end of the string. The incoming string would be processed by the microprocessor to set the parameters of the IGS. The outgoing string would basically acknowledge that the incoming string was accepted, confirm IGS settings or provide raw data/information for processing by the external programmer.

The RAM is used to store information and programs for the IGS. The RAM receives the sensed information about the intrinsic gastric activity from the microprocessor, analyzes that information to determine if the activity is normal according to a selected algorithm(s), and provides that analysis output to the microprocessor to initiate the therapy in accordance with the particular programming selected. Multiple programs may be stored in RAM to establish specific profiles of IGS activation, response, and performance. The RAM may also be used to store various parameters that indicate device performance, gastric activities, and therapies administered.

In use, the preferred embodiment of the invention operates as follows:

The electrodes of the lead(s) would be implanted (laparoscopically or through an open incision) in or on the gastric wall for communication with the circular layer of the gastric smooth muscle (reference FIG. 3). Since the lower portion of the stomach is primarily responsible for solids mixing and motility, the preferred location of the electrodes is the antrum, along the lesser curvature. The lesser curvature is preferable because it does not distend as much as the greater curvature and offers a more stable position. After the lead is secured, the IGS would be connected to the lead(s) and implanted in a subcutaneous or sub-fascial pocket in the patient's abdomen.

Figure 8:
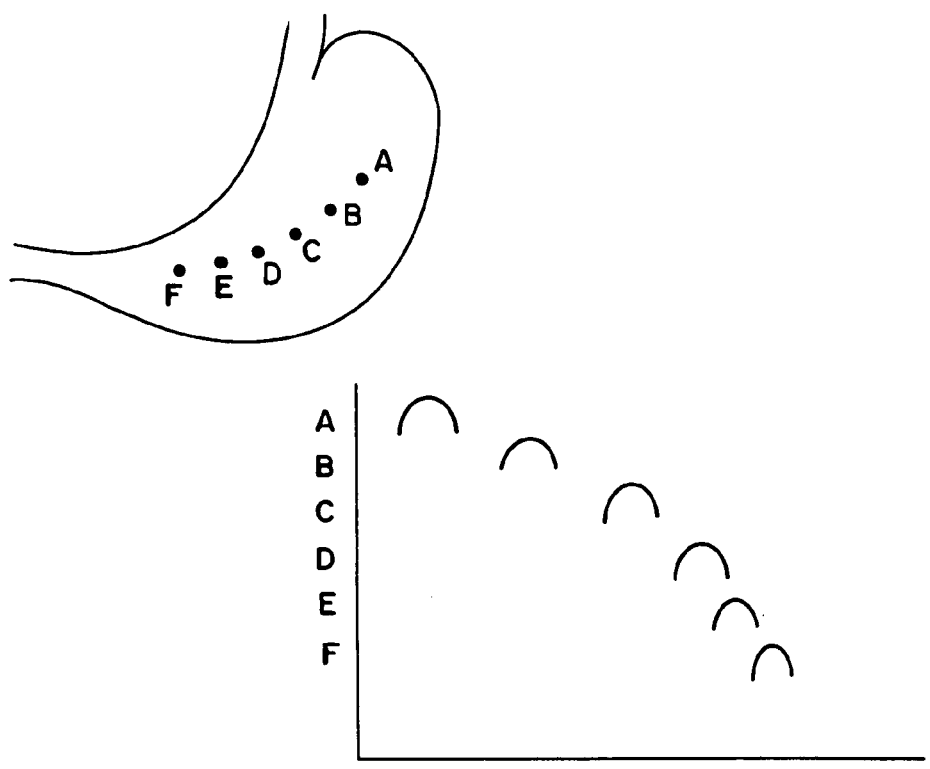
FIG. 8 illustrates the progression of a normal gastric slow wave along the stomach.
Figure 9:
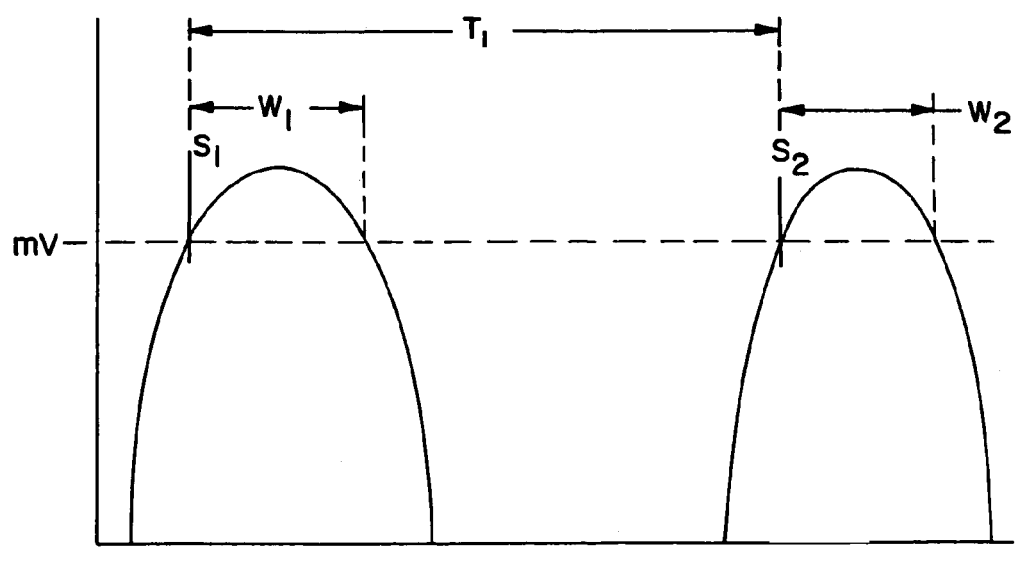
FIG. 9 depicts the discernible features of a gastric slow wave.

Normal gastric electrical activity progresses caudally from the pacemaker area of the fundus towards the pylorus at a rate of approximately 5 mm per second. The activity tends to speed up and organize as it progresses down the antrum. (FIG. 8 depicts the progression of a normal slow wave along the stomach from position A through position F.) The normal activity has pulse amplitudes, pulse widths, and frequency (intervals) that are discernible from abnormal activity. FIG. 9 depicts the discernible parameters that can be utilized to identify/classify the slow wave.

Figure 10:
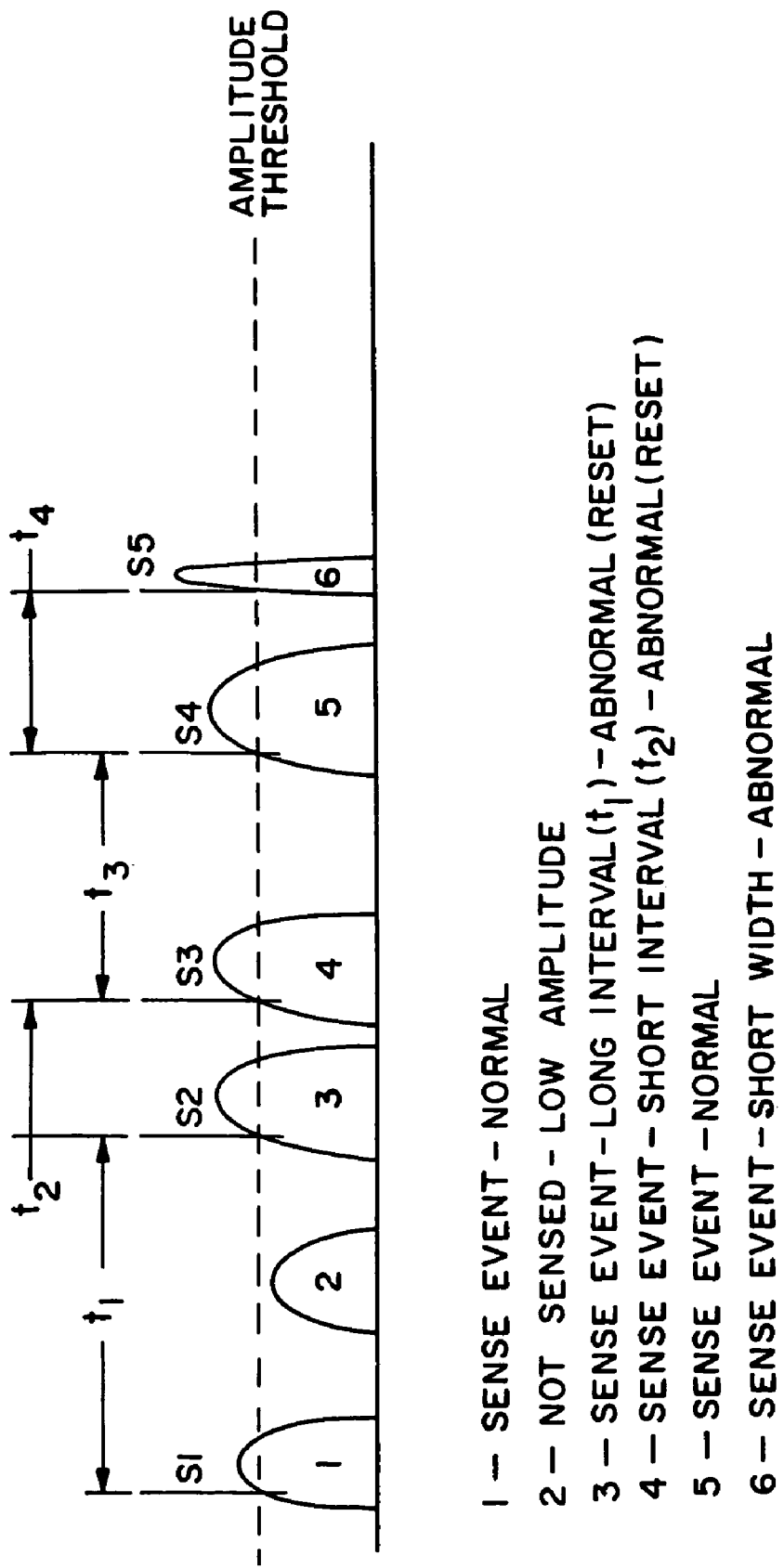
FIG. 10 illustrates identification/classification of normal and abnormal gastric activity.

As the intrinsic activity crosses an implanted electrode, the depolarization of the cells will impart an electrical potential on that electrode (differentially compared to a second electrode in an area not undergoing depolarization). If the two electrodes have been programmed to serve as sensing electrodes, the electric potential is conveyed to the sensing circuitry. There it is filtered and amplified and presented to the information processor. The information processor (in conjunction with any RAM program/algorithm) identifies/classifies the activity as normal or abnormal. FIG. 10 depicts a string of gastric activity and the potential classification of the waves. If identified as normal, the information processor initiates stimulation as per the programmed parameters. If classified as abnormal, the microprocessor re-initiates sensing. Certain parameters of the intrinsic signal and stimulation are logged into RAM for history and for use in other algorithms.

An alternative embodiment of the invention analyzes the frequency components of the sensed signal for evidence of electrical response activity resulting from a contraction. If the signal contains frequencies that are associated with a contraction, a stronger type of stimulation is invoked to disrupt/disorganize or decouple the contraction.

Figure 11:
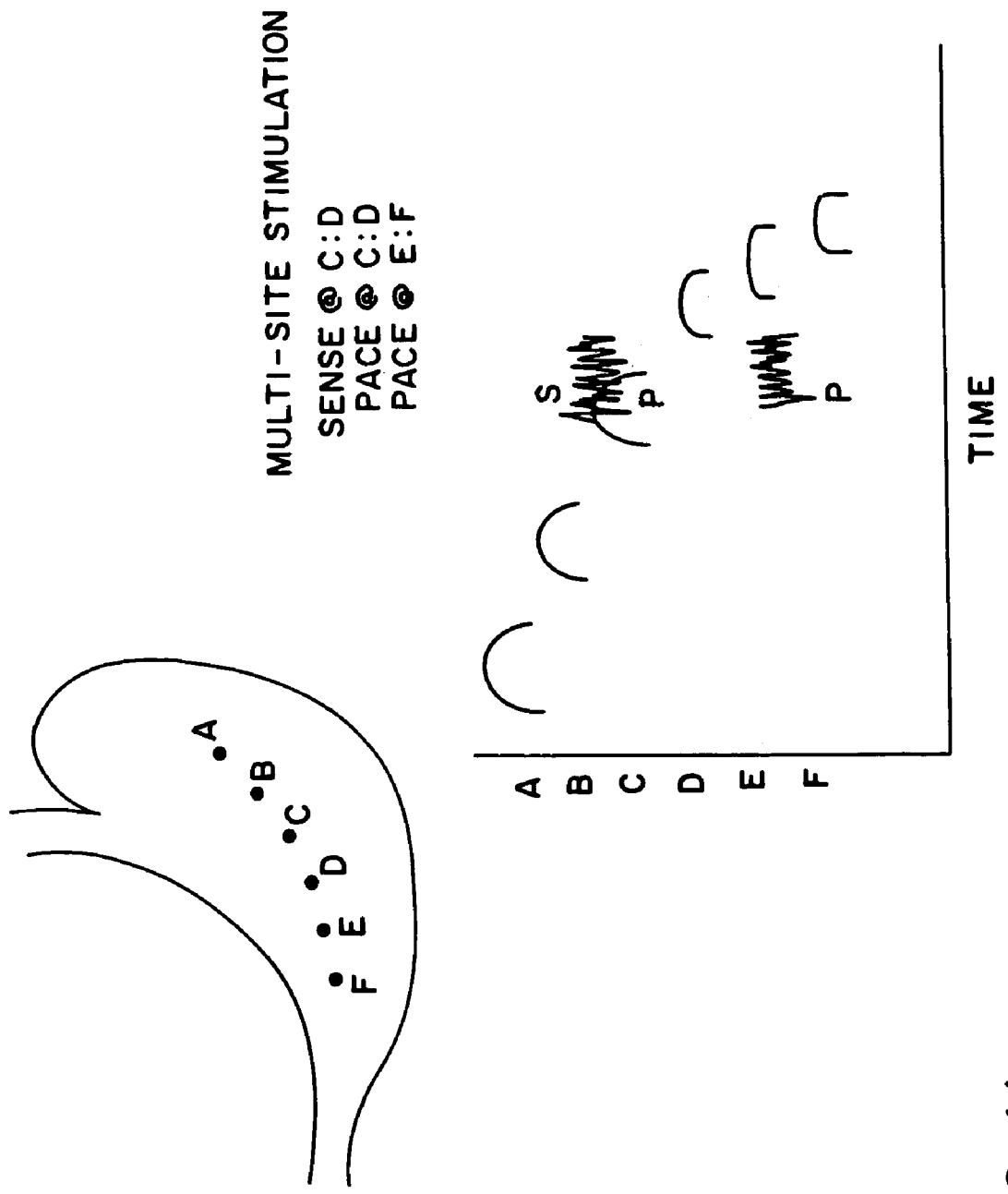
FIG. 11 depicts electrical stimulation at multiple sites.
Figure 12:
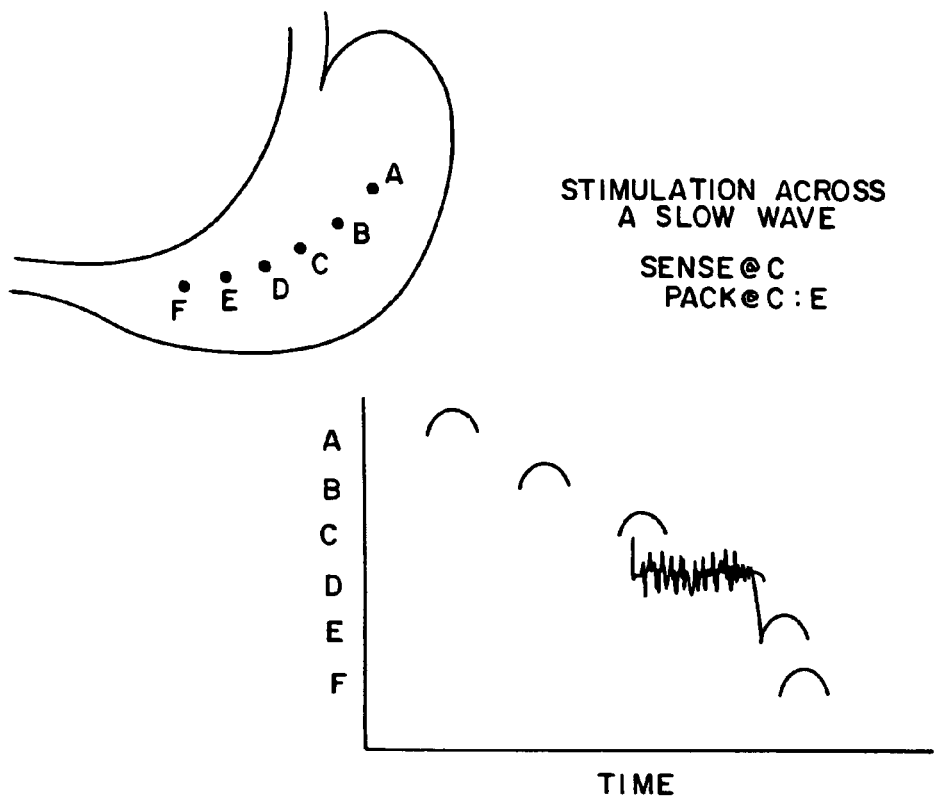
FIG. 12 depicts electrical stimulation across a slow wave.

The preferred embodiment may invoke one or multiple stimulation therapies that are dependent upon the activity sensed and the programmed therapeutic scheme. The stimulation may use electrical pulse trains of equally alternating polarity, electrical pulse trains of asymmetrically alternating polarity, and multiphasic pulses of equal or unequal phase widths. The stimulation may be delivered at a single or a plurality of sites. FIG. 11 depicts stimulation at multiple (two) sites. Additionally the stimulation vector can be switched (at any point) between any single pair of electrodes or plurality of electrodes providing that at least one bipolar pair is selected (reference FIGS. 6 and 7). The stimulation schemes are described as follows:

(a) Stimulation across a slow wave (FIG. 12). Stimulation across a slow wave occurs when the stimulation is applied between electrodes that lie on opposite sides of the slow wave. It is designed to depolarize cells prior to the wave induced depolarization. This will make the cells refractory to the wave and create an attenuation of the slow wave in the area of stimulation. Stimulation across the wave has a disadvantage in that some of the cells involved are already depolarized (as a result of the wave) and energy is wasted on those cells.

Figure 13:
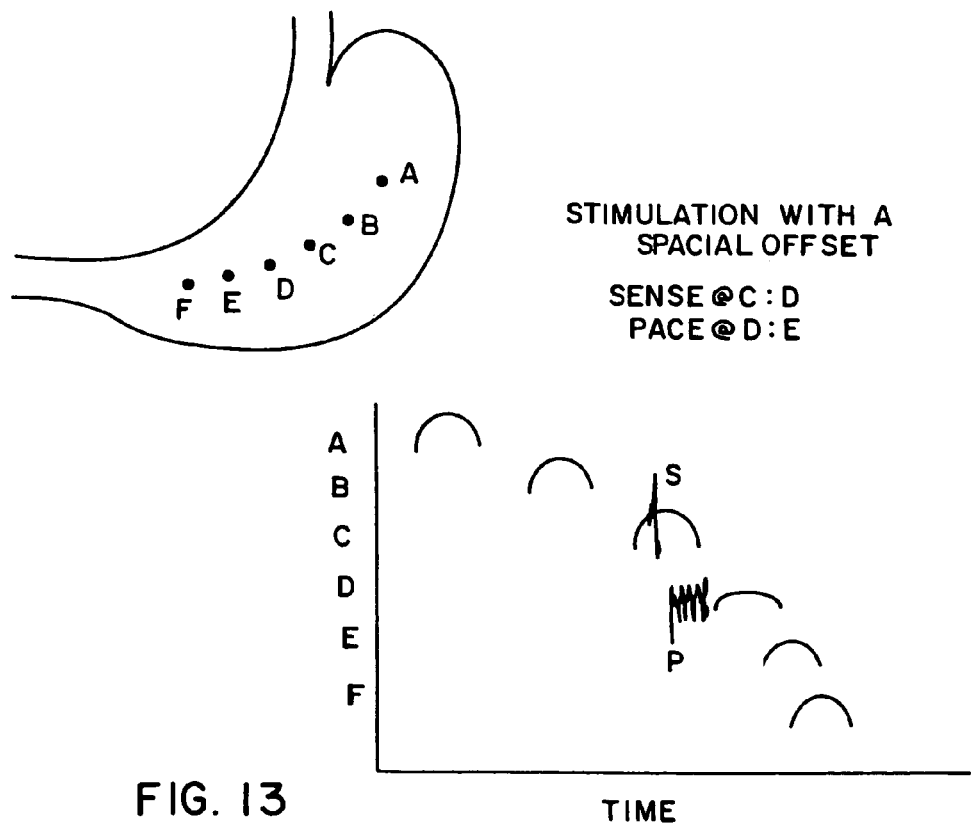
FIG. 13 depicts electrical stimulation with a spatial offset.

(b) Stimulation in advance (spatial offset) of propagation (FIG. 13). Stimulation in spatial advance of the propagating wave affords the advantage of only involving cells that are not part of the wave. The disadvantage is that the degree (length and direction/orientation) of the spatial offset must be considered to ensure that cell repolarization does not occur before the wave arrives. It may require relatively fixed configurations of electrodes placed in relation to the propagation path.

(c) Stimulation in advance (spatial and temporal offsets) of propagation (FIG. 14). Stimulation in advance of wave propagation with a temporal and a spatial offset involves sensing at one location and stimulation at a second location with a programmable delay to ensure that the cells do not repolarize before the wave arrives. It affords the advantage of a spatial offset and does not require precise electrode orientations to achieve the same ends.

Figure 16:
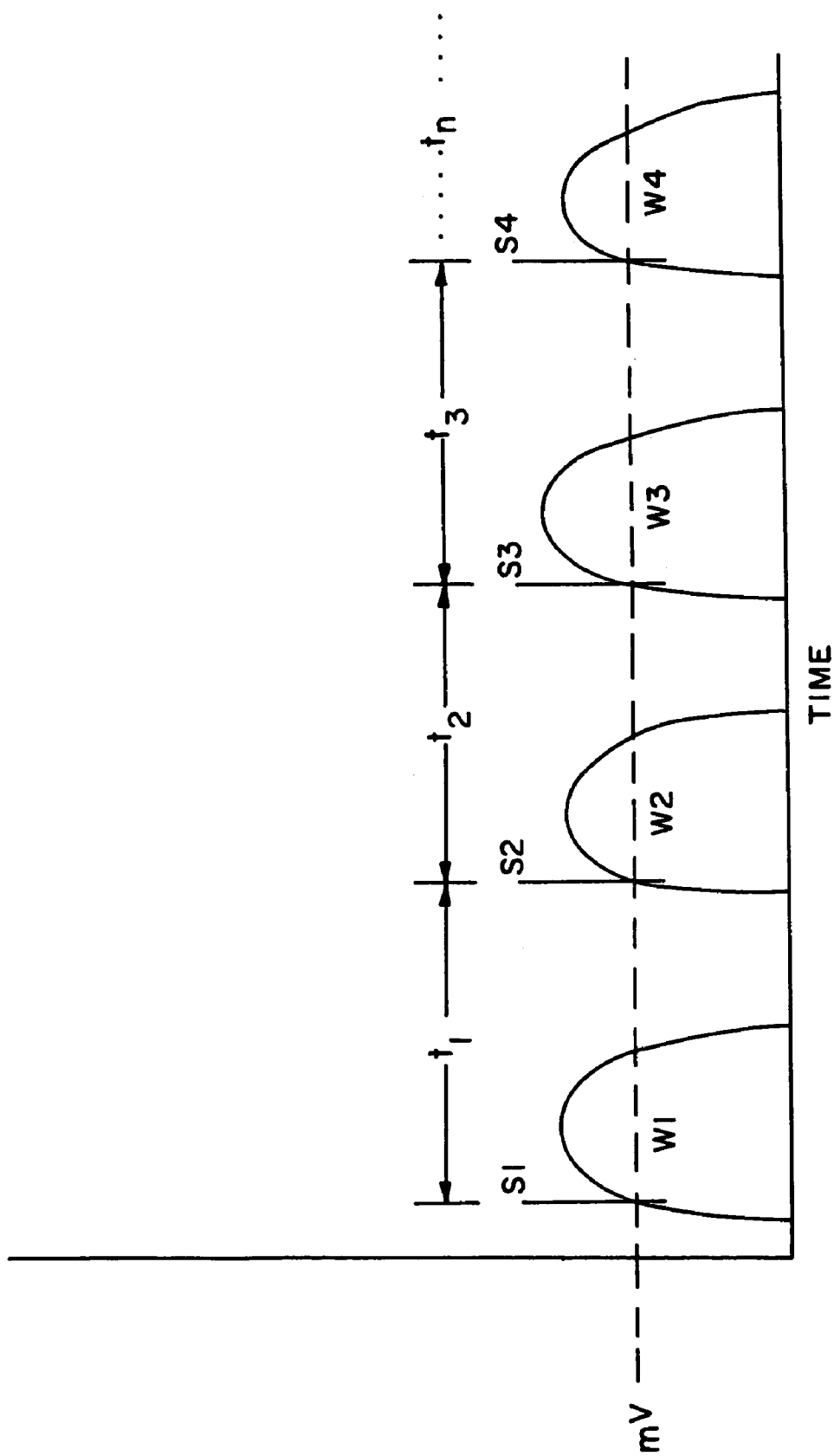
FIG. 16 illustrates the sensing history used to calculate the anticipated interval of the next slow wave.
Figure 17:
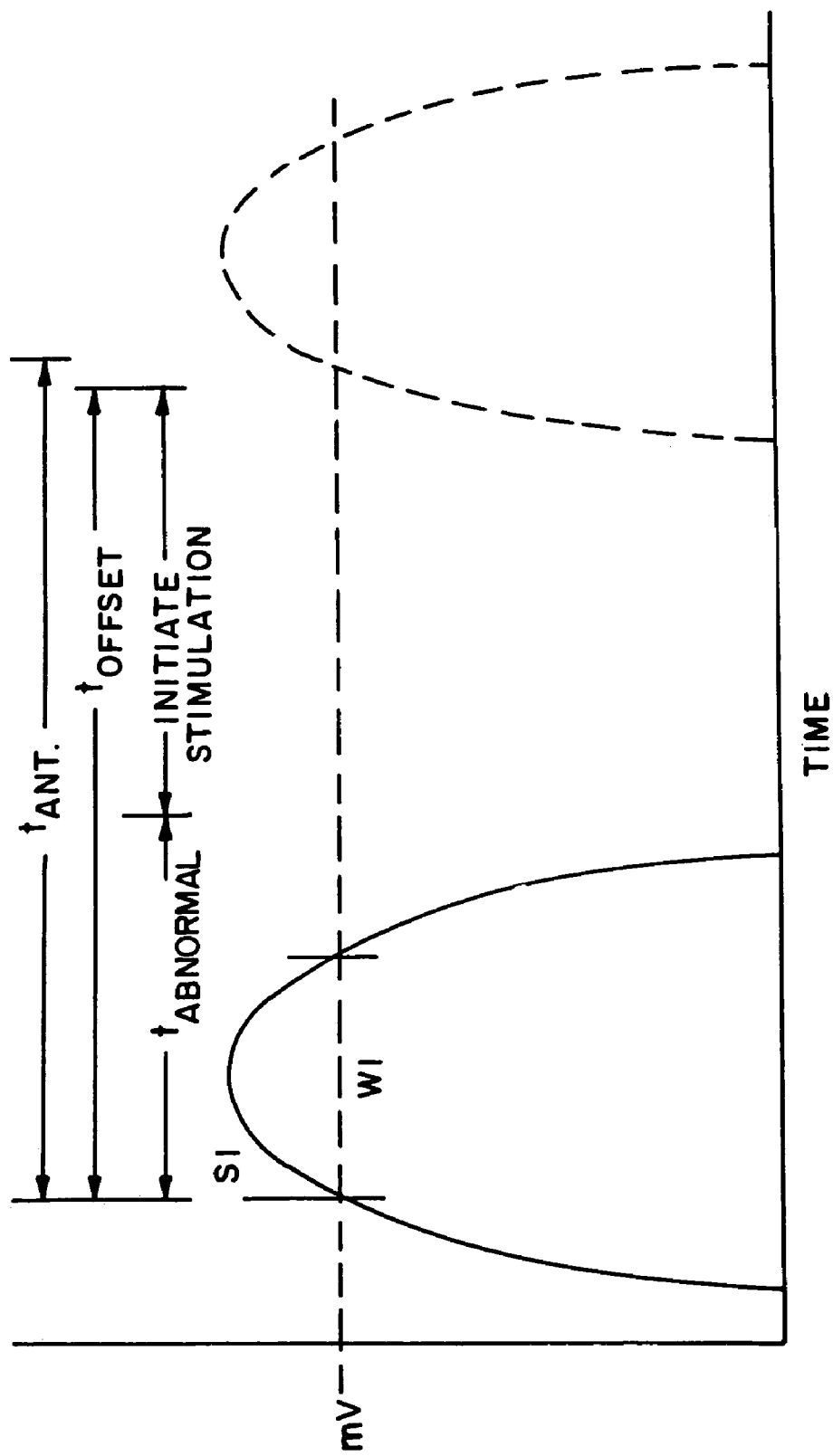
FIG. 17 illustrates the timing of the anticipatory stimulation.

(d) Anticipatory (temporal delay to anticipate the next wave) stimulation (FIG. 15). Anticipatory stimulation involves sensing between a pair of electrodes and delaying the stimulation until just prior to the next normal wave is anticipated. The stimulation may be applied to the sensing electrodes or any set of electrodes upstream from the sensing electrodes. The amount of delay is calculated from the history of normal intervals derived from the sensing identification and parameter storage. FIG. 16 depicts a running history used to calculate the expected interval timing until the next normal slow wave. The calculation would involve averaging a running history of normal intervals and subtracting a small time interval from that average. FIG. 17 depicts the anticipatory stimulation interval timing.

Figure 18:
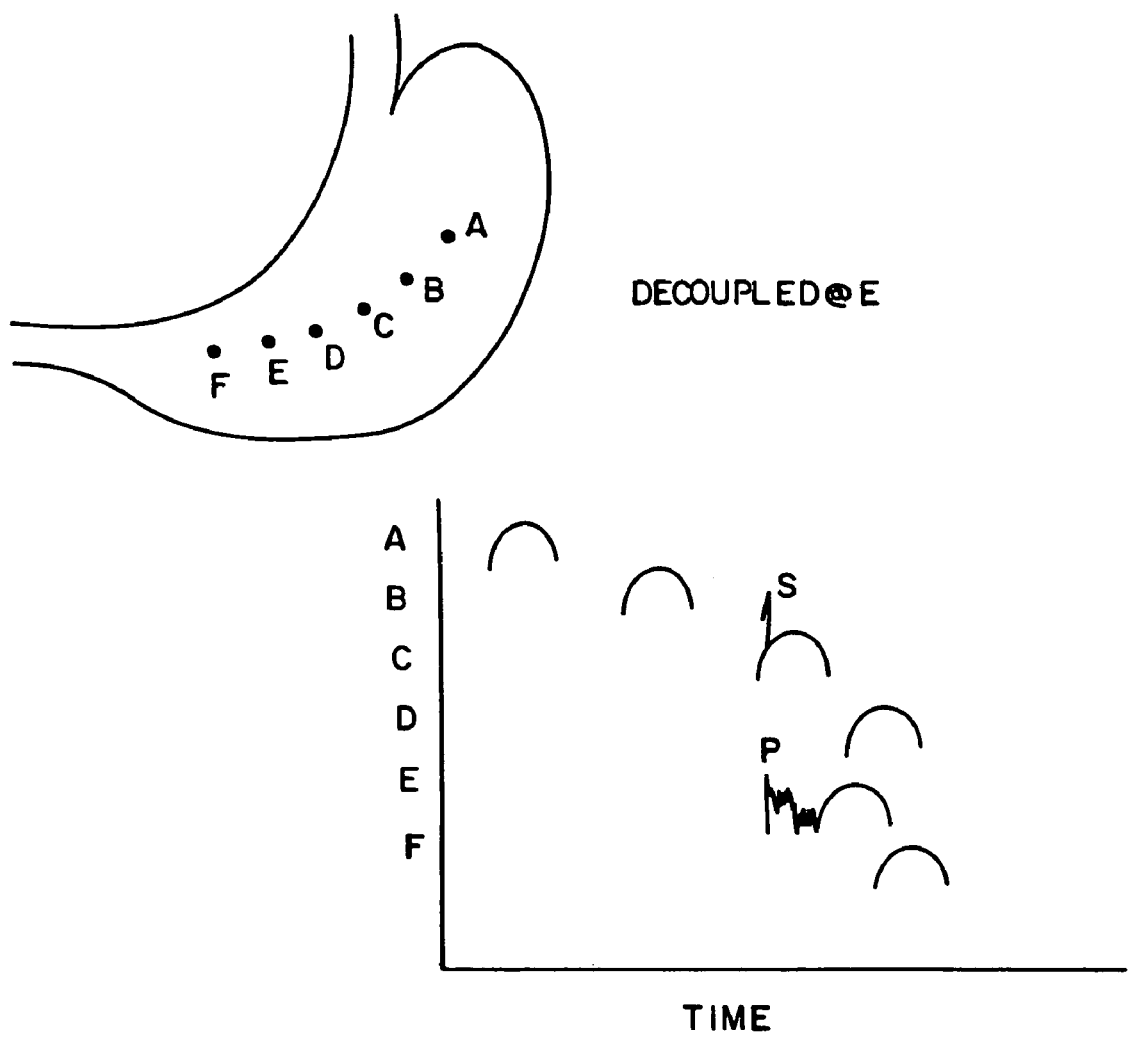
FIG. 18 illustrates decoupling stimulation (triggered by sensing at position C) applied at position E. The decoupling stimulus is intended to initiate an opposing contraction.

(e) Decoupling stimulation (FIG. 18). Decoupling stimulation involves sensing a peristaltic contraction at one location and strong stimulation at a second location to invoke a competing contraction that would propagate towards and away from the intrinsic contraction. Where the two contractions meet, they would tend to cancel each other. The advancing invoked contraction would not have the volume of chyme because it would precede the intrinsic movement and the efficiency of the gastric motility would be reduced.

(f) Ectopic stimulation. Ectopic stimulation involves overriding the intrinsic electrical activity by application of strong stimulation at an interval that is shorter than the intrinsic interval and at a location that does not afford a natural progression of the motility. The preferred location is on the gastric antrum close to the pylorus such that the majority of any propagation would be retrograde.

(g) Combined nerve and gastric stimulation. Combined nerve and gastric stimulation involves application of any of the previously listed therapy schemes with specific stimulation intended to suppress, block, or desensitize the enervation of the stomach. The stimulation could be a combination of pulse trains having neuro and muscular components or separate channels dedicated to the specific neural or muscular waveforms.

Figure 19:
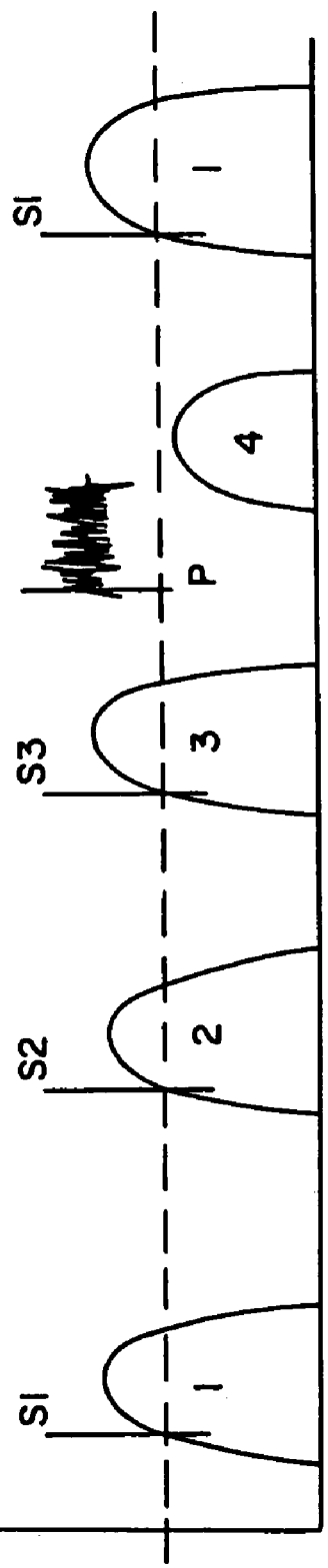
FIG. 19 illustrates proportional stimulation intended to disorganize 25% of the normal slow waves.
Figure 20:
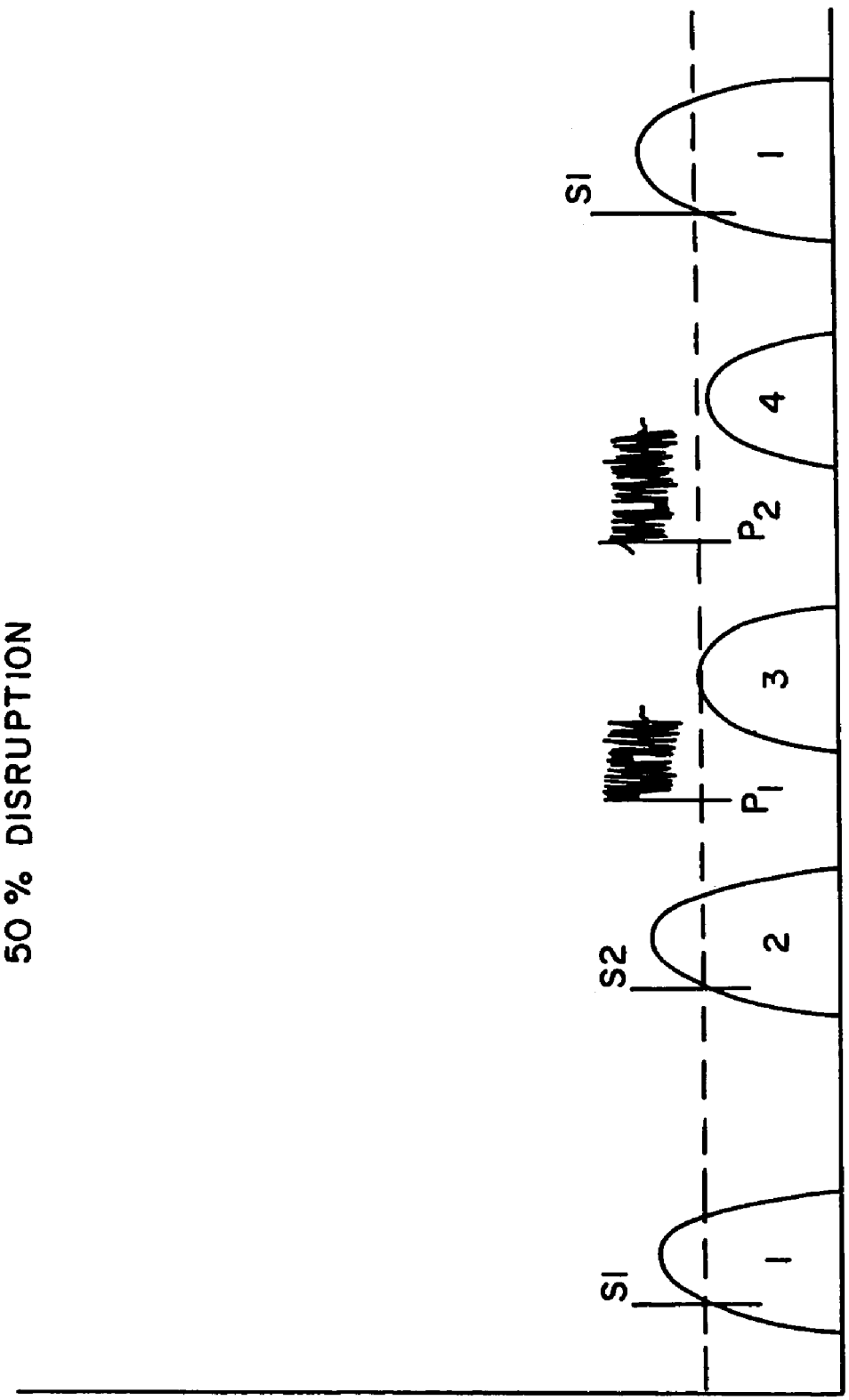
FIG. 20 illustrates proportional stimulation intended to disorganize 50% of the normal slow waves. An alternative embodiment would disrupt every other normal slow wave.

(h) Proportional stimulation. Proportional stimulation is a modulator of any or all of the previous stimulation schemes (except ectopic stimulation). In proportional stimulation, the disruptive, disorganizing, or decoupling stimulation is applied to a programmable percentage of the qualifying (normal) intrinsic activity. FIGS. 19 and 20 depict disorganization of 25% and 50% of the normal slow waves. (An alternative embodiment of FIG. 20 is disorganization of every other normal slow wave.) This type of stimulation allows the physician to modulate the intrinsic activity and still preserve some normal function. In addition, in times of increased abnormal gastric activity (such as when a patient is sick) proportional stimulation will be less frequent due to the decreased quantity of qualifying normal waves.

It should be recognized that the present invention may be used in many different electrophysiological stimulation embodiments, and all such variations or uses are contemplated by the present invention. While there has been described embodiments of the invention with respect to gastric stimulation and sensing, it will be clear that one skilled in the art may employ such in applications beyond the presently described preferred embodiments. Accordingly, it is intended that the scope of the invention, including such alternatives, modifications, and various shall be defined by the appended claims.

What is claimed is:

1. A system for gastric stimulation of a patient comprising:
a plurality of sensing electrodes for sensing intrinsic gastric activity from a stomach wall of a patient;
an implantable gastric stimulator coupled to the plurality of sensing electrodes, the implantable gastric stimulator configured to receive the sensed intrinsic gastric activity and perform an analysis of the sensed intrinsic gastric activity to classify the activity as normal or abnormal, and determine whether to create an electrical stimulation based at least in part upon the classification of the sensed intrinsic gastric activity as normal or abnormal, wherein the implantable gastric stimulator delivers the electrical stimulation when the sensed intrinsic gastric activity is classified as normal;

a plurality of stimulation electrodes configured to convey the electrical stimulation from the implantable gastric stimulator to the stomach wall of the patient, wherein the plurality of stimulation electrodes defines a plurality of stimulation vectors, wherein:
the electrical stimulation is configured to disrupt normal gastric activity of the stomach, and
the implantable gastric stimulator is configured to switch between any of the plurality of stimulation vectors depending upon the sensed intrinsic gastric activity.

2. A system as recited in claim 1, further comprising one or a plurality of elongated lead body sheaths having proximal end connectors for coupling said stimulation and sensing electrodes with said implantable gastric stimulator, portions of said stimulation and sensing electrodes extending through the elongated lead body sheaths to their distal end, the distal end of the elongated lead body sheaths for electrical communication with the stomach wall of the patient and for positioning said stimulation and sensing electrodes on or in the stomach wall.

3. A system as recited in claim 1, wherein said plurality of the stimulation and sensing electrodes are positionable at different locations of the stomach wall.

4. A system as recited in claim 1, wherein the implantable gastric stimulator further comprises a radio frequency telemetry transceiver provided for communication with a remote programmer.

5. A system as recited in claim 1, wherein said implantable gastric stimulator comprises a programmable microprocessor or microcontroller.

6. A system as recited in claim 1, wherein the stimulator temporarily reverts to a power conserve condition at programmable times of the day.

7. A system as recited in claim 1, wherein said sensing electrodes communicate the sensed intrinsic gastric activity to the implantable gastric stimulator for identifying at the implantable gastric stimulator an interval, an amplitude, and a duration of the sensed intrinsic gastric activity.

8. A system as recited in claim 7, wherein said sensing electrodes communicate the sensed intrinsic gastric activity to the implantable gastric stimulator for identifying at the implantable gastric stimulator a frequency spectrum of the sensed intrinsic gastric activity.

9. A system as recited in claim 8, wherein the stimulator analyzes the sensed intrinsic gastric activity and classifies the sensed intrinsic gastric activity as a slow wave or a peristaltic wave.

10. A system as recited in claim 1, wherein the stimulator temporarily reverts to a power conserve condition in the absence of a programmable threshold of normal electrical activity.

11. A system as recited in claim 10, wherein the stimulator delivery of electrical stimulation is triggered by electrical activity classified as a plurality of normal events.

12. A system as recited in claim 11, wherein the stimulator is programmed to deliver electrical stimulation on all or a percentage of the plurality of normal events.

13. A system as recited in claim 12, wherein the electrical stimulation is delivered across the sensed intrinsic gastric activity.

14. A system as recited in claim 12, wherein the electrical stimulation is delivered with a spatial offset to the sensed intrinsic gastric activity.

15. A system as recited in claim 12, wherein the electrical stimulation is delivered with a temporal offset to the sensed intrinsic gastric activity.

16. A system as recited in claim 12, wherein the electrical stimulation is delivered in anticipation of a next normal electrical activity.

17. A system as recited in claim 15, wherein the temporal offset is programmable by a user.

18. A system as recited in claim 1, wherein the stimulator incorporates at least one stimulation channel coupled to the plurality of stimulation electrodes and at least one independently programmable sensing channel coupled to the plurality of sensing electrodes.

19. A system as recited in claim 18, wherein at least one stimulation channel is programmable to parameters associated with nerve stimulation.

20. A system as recited in claim 1, wherein the implantable gastric stimulator employs a neural network to classify the sensed intrinsic gastric activity.

21. A system for gastric stimulation of a patient comprising:
a plurality of sensing electrodes for sensing intrinsic gastric activity from a stomach wall of a patient;
an implantable gastric stimulator coupled to the plurality of sensing electrodes, the implantable gastric stimulator configured to receive the sensed intrinsic gastric activity and perform an analysis of the sensed intrinsic gastric activity to classify the activity as normal or abnormal, and determine whether to create an electrical stimulation based at least in part upon the classification of the sensed intrinsic gastric activity as normal or abnormal, wherein the implantable gastric stimulator delivers the electrical stimulation when the sensed intrinsic gastric activity is classified as normal; and
a plurality of stimulation electrodes configured to convey the electrical stimulation from the implantable gastric stimulator to the stomach wall of the patient, wherein the electrical stimulation is configured to disrupt normal gastric activity of the stomach, wherein:
the stimulator temporarily reverts to a power conserve condition in the absence of a programmable threshold of normal electrical activity, delivers the electrical stimulation when the stimulator classifies sensed electrical activity as a plurality of normal events, is programmed to deliver electrical stimulation on all or a percentage of the plurality of normal events, and is configured to adapt temporal delivery of electrical stimulation based upon an algorithm considering a running history of recent predecessor electrical activity events.

22. A system as recited in claim 21, wherein the polarity of the stimulation electrodes is programmable by a user at the stimulator allowing stimulation between a single pair or a plurality of electrodes.

23. A system as recited in claim 22, wherein the stimulator is programmed to switch the polarity of one or a plurality of the various stimulation electrodes to accommodate multiphase stimulation.

24. A system as recited in claim 23, wherein the electrical stimulation comprises one or a plurality of biphasic pulses programmable within the following parameters, comprising:
pulse amplitude between 0.0 to 15 V or 0.0 to 15 mA;
pulse width between 20 msec to 500 msec;
pulses per event between 1 and 5; and
first phase width between 25 to 100 percent of pulse width.

25. A system as recited in claim 24, wherein the stimulator comprises an array, the array comprising two or more capacitors, and the pulse width is accommodated by switching between the two or more capacitors in the array.

26. A system as recited in claim 25, wherein the electrical stimulation comprises an alternating polarity pulse train programmable within the following parameters, comprising:
pulse amplitude between 0.0 to 15 V or 0.0 to 15 mA;
pulse width between 100 μsec and 750 μsec;
pulses per second (frequency) between 10 to 120 Hz; and
duration of pulse train between 0.5 and 30 seconds.

27. A system as recited in claim 26, wherein the stimulator comprises a memory and the parameters comprising quantities, interval frequency, duration, and amplitude for the sensed events and quantities of paced events are stored in memory for subsequent recall.

28. A system as recited in claim 27, wherein the sensed intrinsic gastric activity can be telemetered from the implantable gastric stimulator to an external programmer to assist in establishing the appropriate stimulation parameters.

29. A method for gastric stimulation of a patient comprising:
sensing intrinsic gastric activity on the stomach wall of a patient;
classifying the sensed intrinsic gastric activity as normal or abnormal;
determining when to apply electrical stimulation to the stomach wall of the patient based upon the classification of the sensed intrinsic gastric activity as normal or abnormal;
selecting at least one of a plurality of stimulation vectors across the stomach wall for application of electrical stimulation based upon the sensed intrinsic gastric activity;
forming an electrical signal in response to the determining when the sensed intrinsic gastric activity is classified as normal; and
applying the electrical signal via the at least one selected stimulation vector to disrupt normal gastric activity of the stomach.

30. The method of claim 29 further comprising maintaining a history of predecessor electrical events.

31. The method of claim 29 further comprising analyzing the sensed intrinsic gastric activity and classifying the sensed intrinsic gastric activity as a slow wave or a peristaltic wave.

32. The method of claim 29 wherein the step of determining determines a percentage of normal events and the step of disrupting applies the electrical signal for the percentage of electrical events.

33. The method of claim 29, wherein the step of applying is triggered by electrical activity classified as normal.

34. A system comprising:
a plurality of sensing electrodes for sensing intrinsic electrical gastric activity from a stomach wall of a patient;
an implantable gastric stimulator coupled to the sensing electrodes, wherein the implantable gastric stimulator receives the sensed intrinsic electrical gastric activity and classifies the activity as normal or abnormal, and wherein the stimulator creates electrical stimulation when the sensed intrinsic electrical gastric activity is classified as normal; and
a plurality of stimulation electrodes for conveying the electrical stimulation from the implantable gastric stimulator to the stomach wall of the patient, wherein the plurality of stimulation electrodes defines a plurality of stimulation vectors, wherein:
the electrical stimulation is configured to disrupt normal gastric activity of the stomach; and
the implantable gastric stimulator is configured to switch between any of the plurality of stimulation vectors based on the sensed intrinsic electrical gastric activity.

35. A method comprising:
sensing intrinsic electrical gastric activity from a stomach wall of a patient;
classifying the intrinsic electrical gastric activity as normal or abnormal;
selecting at least one of a plurality of stimulation vectors across the stomach wall for application of electrical stimulation to the patient based upon the sensed intrinsic electrical gastric activity;
applying electrical stimulation to the patient via the at least one selected stimulation vector when the intrinsic electrical gastric activity is classified as normal, wherein the electrical stimulation is configured to disrupt normal gastric activity of the stomach; and
withholding application of electrical stimulation to the patient when the intrinsic electrical gastric activity is classified as abnormal.

\* \* \* \* \*